United States Patent [19]

Hopper et al.

[11] Patent Number: 5,251,347
[45] Date of Patent: Oct. 12, 1993

[54] BED HAVING PATIENT WARMING APPARATUS

[75] Inventors: Christopher J. Hopper, Oshtemo Township, Kalamazoo County; Louis A. Haddock, Jr., Emmett Township, Calhoun County; John S. Messner, Battle Creek; Larry W. Gardner, Kalamazoo Township, Kalamazoo County, all of Mich.

[73] Assignee: Stryker Corporation, Kalamazoo, Mich.

[21] Appl. No.: 816,557

[22] Filed: Jan. 3, 1992

[51] Int. Cl.⁵ .................................................. A61G 7/00
[52] U.S. Cl. .................................... 5/423; 5/284; 5/469; 607/107; 607/111
[58] Field of Search .................... 5/284, 421, 423, 453, 5/455, 468, 469; 128/376, 400

[56] References Cited

U.S. PATENT DOCUMENTS

| | | |
|---|---|---|
| 10,139 | 10/1853 | Scott . |
| 613,328 | 11/1898 | Shryock . |
| 1,142,876 | 6/1915 | Davis et al. . |
| 2,093,834 | 9/1937 | Gaugler . |
| 2,110,022 | 3/1938 | Kliesrath . |
| 2,235,966 | 3/1941 | Summers . |
| 2,462,984 | 3/1949 | Maddison . |
| 2,493,067 | 1/1950 | Goldsmith . |
| 2,512,559 | 6/1950 | Williams . |
| 2,585,517 | 2/1952 | Tolen . |
| 2,601,189 | 6/1952 | Wales, Jr. . |
| 2,695,413 | 11/1954 | TerMaat ........................... 5/469 X |
| 2,706,988 | 4/1955 | Weber . |
| 3,230,556 | 1/1966 | Shippee . |
| 3,266,064 | 8/1966 | Figman . |
| 3,418,726 | 12/1968 | Sparks . |
| 3,444,922 | 5/1969 | Dingman . |
| 3,529,310 | 9/1970 | Olmo . |
| 3,644,950 | 2/1972 | Lindsay, Jr. ........................ 5/469 X |
| 3,667,073 | 6/1972 | Renfroe ............................. 5/453 X |
| 3,738,367 | 6/1973 | Hardy . |
| 3,757,366 | 9/1973 | Sacher . |
| 3,778,851 | 12/1973 | Howorth . |
| 3,881,477 | 5/1975 | Von Otto . |
| 3,908,655 | 9/1975 | Lund . |
| 3,928,876 | 12/1975 | Starr . |

(List continued on next page.)

FOREIGN PATENT DOCUMENTS

| | | | |
|---|---|---|---|
| 7211069 | 7/1973 | Netherlands ........................... | 5/469 |
| 8804548 | 6/1988 | PCT Int'l Appl. ..................... | 5/421 |
| 2213388 | 8/1989 | United Kingdom ................... | 5/284 |

OTHER PUBLICATIONS

Cincinnati Sub-Zero Products, Inc., product brochure for Blanketrol ® and Maxi-Therm Hyper-Hypothermia Systems.
Gaymar Industries, Inc., product brochure for Medi--Therm ®, hypothermia system.
Adel (a wholly owned subsidiary of Stryker), product brochure for Infant Warmer.

Primary Examiner—Michael F. Trettel
Attorney, Agent, or Firm—Flynn, Theil, Boutell & Tanis

[57] ABSTRACT

A hospital bed has an articulated patient support surface with four air outlet housings mounted thereon at spaced locations. An air supply arrangement supplies temperature-controlled air to an air outlet opening in each of the housings. Associated with each housing is an elongate tubular fabric diffusion member having an O-ring which encircles one end thereof and is removably received in a circumferential groove in the air outlet opening. Each diffusion member can be tucked completely into its housing when not in use. Each housing has a cap movable between open and closed positions with respect to the air outlet opening, and an arrangement yieldably urging the cap toward its closed position. A valve arrangement is provided below two of the housings in order to automatically discharge fluids which happen to enter the air supply system through the air outlet openings. In a variation, two of the elongate diffusion members can be replaced with an inflatable underlay or overlay having two inlet sleeves with O-rings which are each releasably coupled to a respective one of the air outlet devices.

71 Claims, 10 Drawing Sheets

U.S. PATENT DOCUMENTS

| | | | |
|---|---|---|---|
| 4,057,861 | 11/1977 | Howorth | 5/468 |
| 4,218,791 | 8/1980 | Itoku . | |
| 4,398,535 | 8/1983 | Guibert . | |
| 4,481,686 | 11/1984 | Lacoste . | |
| 4,525,885 | 7/1985 | Hunt et al. | 5/455 X |
| 4,572,188 | 2/1986 | Augustine et al. . | |
| 4,638,519 | 1/1987 | Hess . | |
| 4,660,388 | 4/1987 | Greene, Jr. . | |
| 4,777,802 | 10/1988 | Feher . | |
| 4,797,962 | 1/1989 | Goode . | |
| 4,867,230 | 9/1989 | Voss . | |
| 4,884,304 | 12/1989 | Elkins . | |
| 4,907,308 | 3/1990 | Leininger et al. . | |
| 4,944,060 | 7/1990 | Peery et al. . | |
| 4,949,412 | 8/1990 | Goode . | |
| 4,959,877 | 10/1990 | Covil . | |
| 5,044,364 | 9/1991 | Crowther . | |
| 5,165,400 | 11/1992 | Berke | 128/400 |

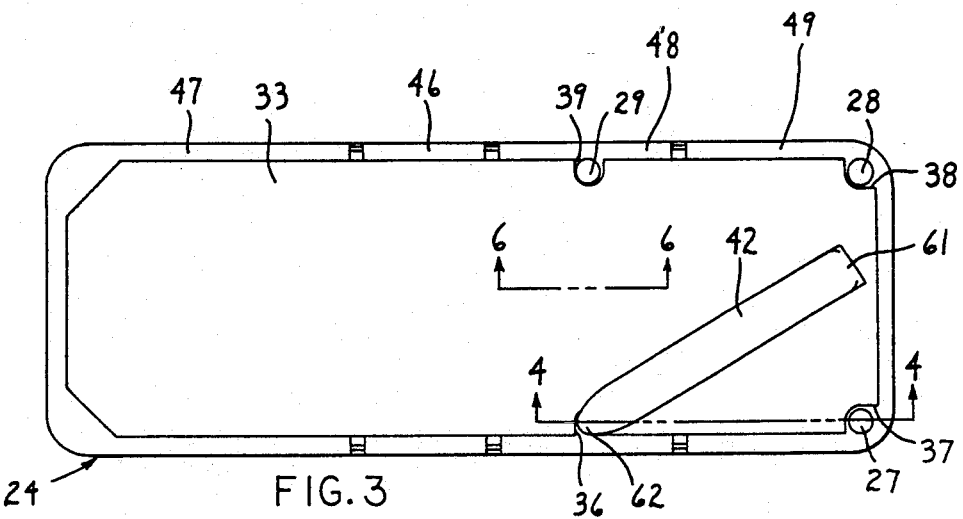
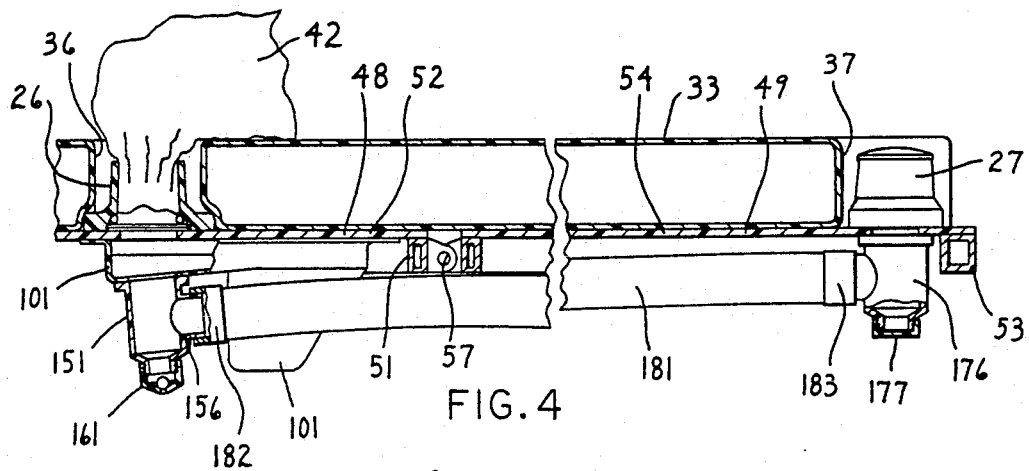
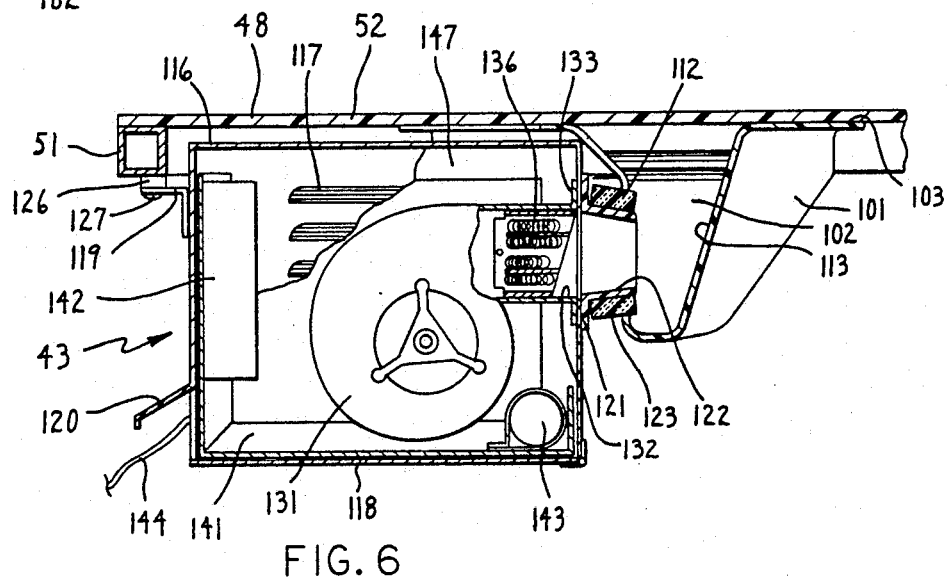

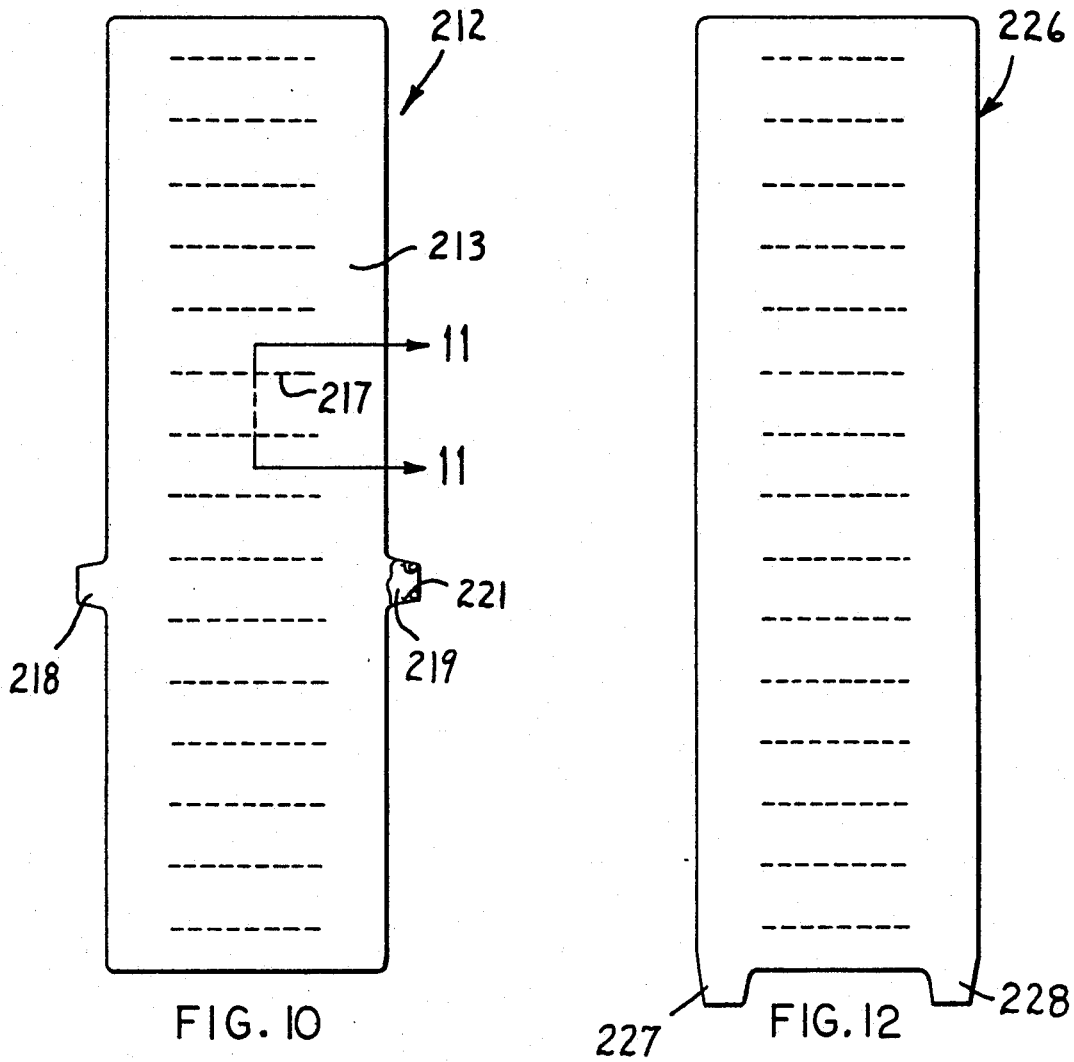
FIG. 10
FIG. 12
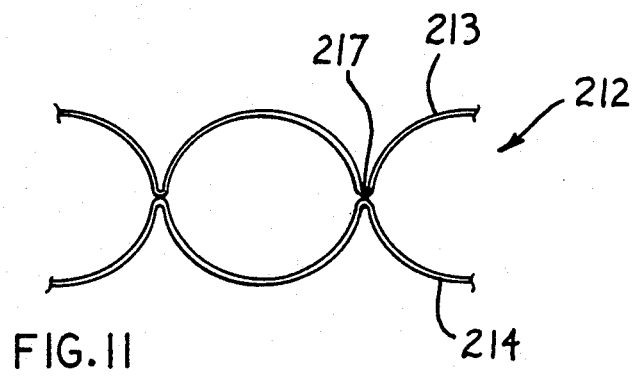
FIG. 11

BED HAVING PATIENT WARMING APPARATUS

FIELD OF THE INVENTION

The present invention relates to a hospital bed and, more particularly, to a hospital bed having the capability to supply temperature-controlled air to a patient.

BACKGROUND OF THE INVENTION

There are certain circumstances in which it is desirable to supply temperature-controlled air to a hospital patient. For example, where a patient has had surgery, the after effects of the anesthesia may include chills. Therefore, in a recovery room, it is common to take certain steps to attempt to warm the patient, for example by placing a pre-warmed blanket over the patient. In other situations, it may be desirable to supply hot or cold air to a particular localized area such as the feet, ankles or knees of a patient.

A number of devices have previously been developed to supply temperature-controlled air to a patient. While these arrangements have generally been satisfactory for their intended purposes, they have not been satisfactory in all respects. Accordingly, one object of the invention is to provide a hospital bed designed to provide temperature-controlled air to a patient in an efficient and reliable manner.

A further object is to provide such a bed having at least one air diffusion member capable of supplying temperature-controlled air to a very localized area.

A further object is to provide such a bed in which an air diffusion member can be easily and quickly detached and reattached, and can be easily cleaned and/or treated with a fungicide and a bactericide.

A further object is to provide such a bed which is designed to minimize the chance of liquids such as water or blood entering the air supply system, and which is designed to be capable of automatically discharging liquids which do manage to enter the air supply system, and to effect such discharge without interrupting normal operation.

A further object is to provide such a bed having an air supply system which is mounted directly on the bed but does not impart significant vibrations to the bed and is otherwise capable of quiet operation.

A further object is to provide such a bed in which the diffusion member can be stored directly on the bed in a very small and compact space when not in use.

A further object is to provide such a bed in which a diffusion member can be supplied with air from any of several different locations on the bed.

A further object is to provide such a bed in which the patient support surface is capable of articulation to various positions without any degradation in the ability to supply temperature-controlled air to the patient on the bed.

A further object is to provide such a bed which is capable of satisfactory operation with a variety of diffusion members designed for different situations.

SUMMARY OF THE INVENTION

The objects and purposes of the invention, including those set forth above, are met according to one form of the invention by providing: a bed having an upwardly facing support surface; an air outlet device mounted on the bed; an elongate diffusion member having a proximate end operationally coupled to said air outlet device, said elongate diffusion member being movable to a plurality of positions with respect to the support surface; and an air supply arrangement coupled to the air outlet device for supplying air to the proximate end of the diffusion member through the air outlet device, the air supplied to the diffusion member being diffused by the diffusion member into a region adjacent and external to the diffusion member.

A different form of the present invention involves the provision of: a bed having an upwardly facing support surface; an air outlet device mounted on the bed and having therein an air outlet opening, the air outlet opening having in an inner surface thereof a circumferential groove; an air supply arrangement coupled to the air outlet device for supplying thereto air which is then emitted through the air outlet opening; and a diffusion member having a tubular air inlet portion which includes an open outer end encircled by a flexible annular retaining member removably disposed in the groove of the air outlet device.

Still another form of the invention involves the provision of: a bed having an upwardly facing support surface; an air outlet device mounted on the bed and having therein an air outlet opening; an air supply arrangement for supplying air to the air outlet opening in the air outlet device; and a diffusion member coupled to the air outlet device for receiving air through the air outlet opening therein and for diffusing the air to a region adjacent and external to the diffusion member, wherein for storage the diffusion member can be tucked substantially in its entirety into the air outlet opening in the air outlet device.

Yet another form of the present invention involves the provision of: a bed having an upwardly facing support surface; an air outlet device mounted on the bed and having therein an air outlet opening, the air outlet device having thereon a cap movable between open and closed positions in which the cap respectively permits and obstructs air flow through the air outlet opening, the air outlet device further including an arrangement for yieldably urging movement of the cap toward its closed position; and an air supply arrangement for supplying air to the air outlet opening in the air outlet device.

A different form of the present invention involves the provision of: a bed having an upwardly facing support surface; an air outlet device mounted on the bed and having therein an approximately vertically extending air outlet opening; an air supply arrangement for supplying air to the air outlet opening for discharge through an upper end thereof; and a valve provided below said air outlet device and communicating with a lower end of said air outlet opening, said valve having a fluid outlet opening and having an arrangement for facilitating a discharge of fluid disposed within the valve through the fluid outlet opening and for resisting the escape of air from the interior of the valve through the fluid outlet opening.

A further form of the present invention involves the provision of: a bed having a support member which has thereon an upwardly facing support surface; first and second air outlet devices mounted at spaced locations on the support member, each air outlet device having therein an air outlet opening; a plenum fixedly secured to the support member and having therein an air channel which is in fluid communication with the air outlet opening in each of the air outlet devices; and an air supply arrangement for supplying air to the plenum.

Still another form of the invention involves the provision of: a bed having an upwardly facing support surface; two air outlet devices mounted on the bed at spaced locations; an air supply arrangement for supplying air to each of the air outlet devices; and a diffusion member having two inlet portions which are each coupled to a respective one of the air outlet devices for receiving therefrom air from the air supply arrangement, the diffusion member diffusing the air supplied thereto to a region adjacent and external to the diffusion member.

BRIEF DESCRIPTION OF THE DRAWINGS

Preferred embodiments of the present invention are described in detail hereinafter with reference to the accompanying drawings, in which:

FIG. 3 is a top view of the bed of FIG. 1;

FIG. 4 is sectional view taken along the line 4—4 of FIG. 3;

FIG. 6 is a sectional view taken along the line 6—6 in FIG. 3 and showing an air supply system of the bed;

FIG. 10 is a fragmentary top view of an underlay according to the invention which can be used with the bed of FIG. 1 in place of a mattress and a diffusion member which are components of the bed of FIG. 1;

FIG. 11 is a sectional view taken along the line 11—11 in FIG. 10;

FIG. 12 is a top view of an overlay according to the invention which can be used with the bed of FIG. 1 in place of a mattress and a diffusion member which are components of the embodiment of FIG. 1;

DETAILED DESCRIPTION

Figure 1:
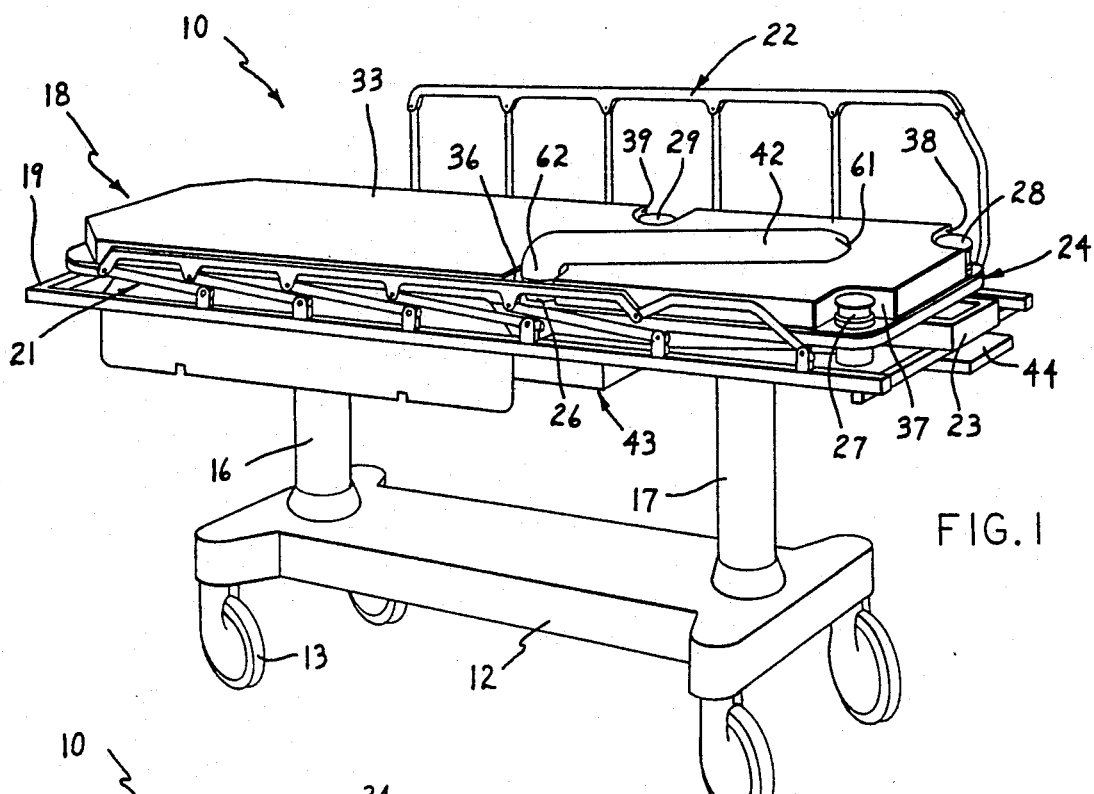
FIG. 1 is a perspective view of a mobile hospital bed embodying the present invention.

FIG. 1 depicts a hospital stretcher or bed 10 which includes a conventional base 12 movably supported on wheels 13, conventional pedestals 16 and 17 extending upwardly from the base 12, and a litter assembly 18 supported on the upper ends of the pedestals 16 and 17.

The litter assembly 18 includes an approximately rectangular lower frame 19, and two conventional collapsible side rails 21 and 22 supported on opposite sides of the lower frame 19. An approximately rectangular upper frame 23 is supported on the lower frame 19 between the guide rails 21 and 22, and supported on the upper frame 23 is an articulated patient support assembly which is described in more detail below. The patient support assembly 24 has secured thereto at spaced location four air outlet housings 26-29.

A mattress 33 removably rests on the upper side of the patient support assembly 24, and has four cutouts 36-39 which each receive a respective one of the air outlet housings 26-29. The mattress 33 is of generally conventional construction and includes a foam core disposed within a plastic cover. The upper surface of the mattress 33 is slightly higher than the tops of the air outlet housings 26-29. An elongate air diffusion member 42 has one end coupled to the housing 26 in FIG. 1, and will be discussed later. An air supply system shown at 43 supplies air to the housings 26-29 in a manner described in more detail later, and a control panel 44 is provided at one end of the stretcher in order to permit hospital personnel to control the air supply system 43.

Figure 2:
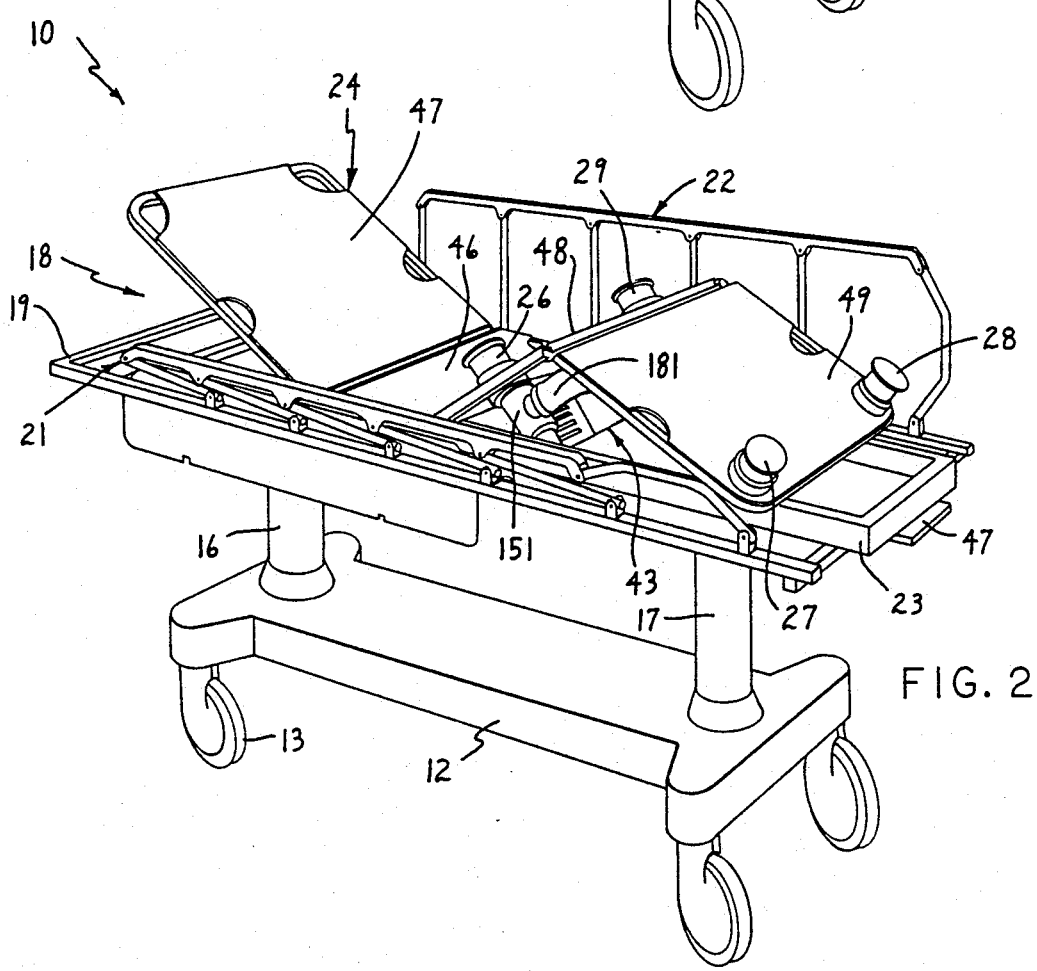
FIG. 2 is a perspective view of the bed of FIG. 1, but in a different operational position and with a mattress and diffusion number omitted for clarity.

Referring now to FIG. 2, in which the mattress 33 is omitted for clarity, the patient support assembly 24 includes a center section 46 which is fixedly coupled to the upper frame 23, a head section 47 which is coupled to one side of the center section 46 for pivotal movement relative thereto about a horizontal axis between inclined and horizontal positions, a thigh section 48 which is pivotally coupled to the opposite side of the center section 46 for pivotal movement relative thereto about a further horizontal axis between inclined and horizontal positions and a foot section 49 which is coupled to the opposite side of the thigh section 48 for pivotal movement about a further horizontal axis. The head section 47, thigh section 48 and foot section 49 are all shown in inclined positions in FIG. 2, and are all in their horizontal positions in FIG. 1. The mechanisms which effect movement of the head section 47, thigh section 48 and foot section 49 are completely conventional and not a part of the present invention, and have therefore been omitted from the drawings for purposes of clarity.

Each of the sections 46-49 of the patient support assembly 24 includes an approximately rectangular frame defining the perimeter of the section, and includes a support board having its peripheral edges secured to the frame. For example, with reference to FIGS. 4 and 7, the thigh section 48 has a rectangular frame 51 made of tubular members, and has a support board 52 with its peripheral edges secured to the frame by not-illustrated screws or rivets. Similarly, as shown in FIG. 4, the foot section 49 has a rectangular frame 53 and a support board 54. The frames 51 and 53 each have outwardly projecting metal tabs which are pivotally coupled at 57 by a horizontal bolt or rivet in order to effect the pivotal coupling between the thigh section and foot section.

Figure 5:
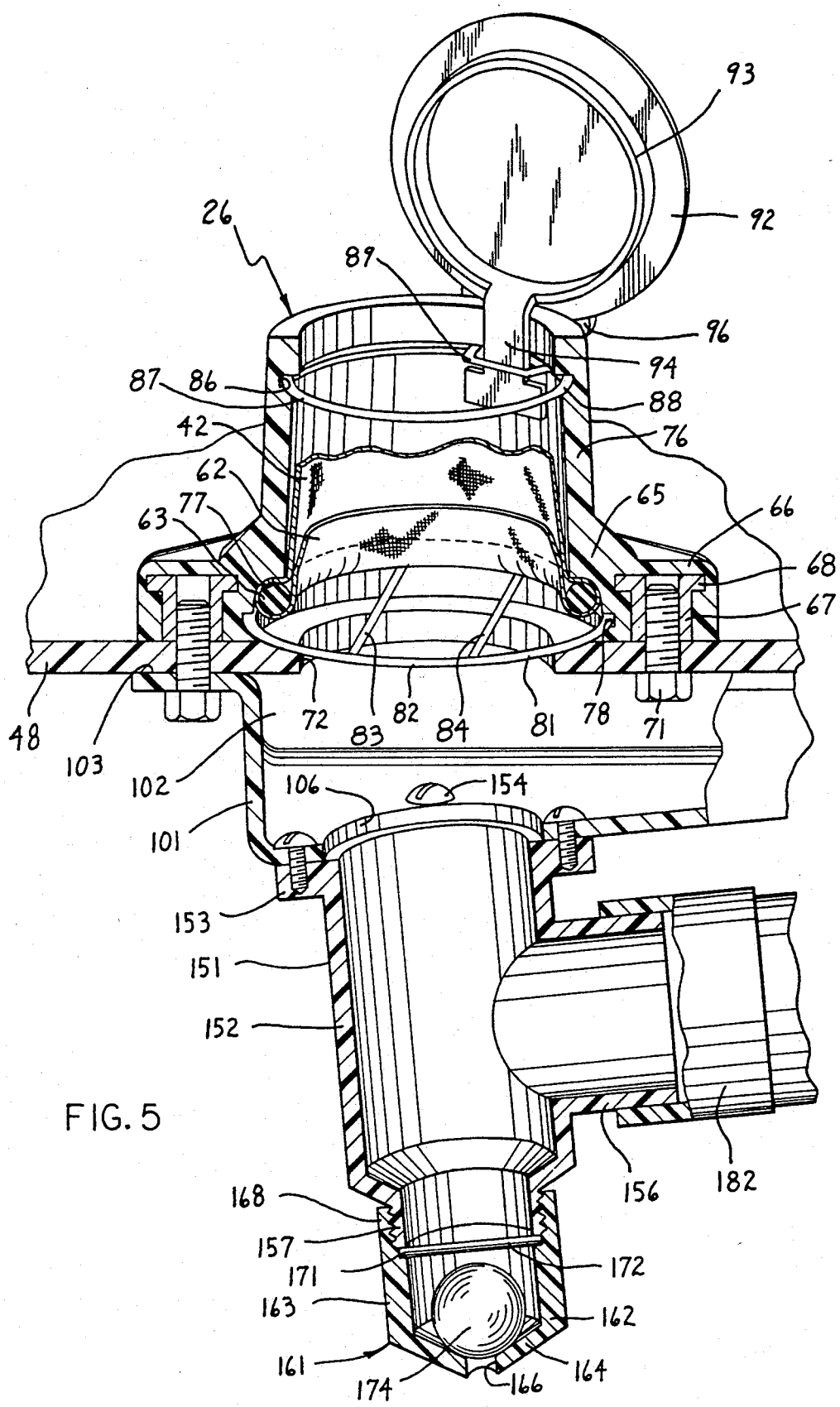
FIG. 5 is a sectional view similar to a portion of FIG. 4 but in an enlarged scale.

Referring to FIGS. 1 and 3, the air diffusion member 42 is an elongate tubular member made of fabric. In the preferred embodiment, the fabric is a tightly woven polyester which is soft and washable, and which has been treated in a conventional manner with conventional fungicidal and bactericidal agents. Air supplied to the air diffusion member 42 from the housing 26 is defused through the fabric in a relatively uniform manner along the length of the air diffusion member 42. The outer end 61 of the air diffusion member 42 is closed by a seam or the like. As best shown in FIG. 5, the opposite end 62 of the air diffusion member 42 has a hem sewn in, and disposed within the hem is a conventional annular rubber O-ring 63.

The housing 26 will now be described in detail. The housings 27-29 are identical to the housing 26, and the explanation of housing 26 is thus equally applicable to them. Referring to FIG. 5, housing 26 includes an annular rubber base portion 65 having two integral and outwardly projecting tabs 66 on opposite sides thereof. Each tab 66 has embedded therein a threaded cylindrical metal nut 67, each nut having at its upper end an outwardly projecting annular flange 68 which resists axial extraction of the nut 67 from the tab 66. A not-illustrated wire frame embedded in the base portion 65 is welded to each of the nuts 67. Bolts 71 extend through openings in the thigh section 48 and threadedly engage the nuts 67 so as to fixedly secure the housing 26 on the upper side of the thigh section 48 with base portion 65 concentrically encircle a circular hole 72 provided through the thigh section 48. A cylindrical tubular upper portion 76 extends upwardly from and is integral with the base portion 65. The upper portion 76 is designed to have some flexibility, and can thus resiliently yield if forces are applied to it, for example where a patient inadvertently sits on the adjacent portion of the mattress and thus puts weight onto the housing.

Provided in an inner surface of the base portion 65 is an annular recess or groove 77, which can receive the end 62 of the air dispersion member 42 having therein the O-ring 63. Just below the groove 77 is a further annular groove 78, which receives a wire grid 81. In particular, the wire grid 81 includes a circular outer wire portion 82 which is disposed in the groove 78, and two spaced, parallel cross wires 83 and 84 which extend between opposite sides of the circular portion 82.

A small distance below the upper end of the cylindrical upper portion 76 is a further annular groove 86, which receives a wire cap retainer 87. The cap retainer 87 includes a circular outer wire 88 which is received in the groove 86, and a U-shaped retaining wire 89 which has the outer ends of its legs fixedly secured to the circular wire 88 and which extends a short distance radially inwardly into the interior of the housing.

The housing includes a disk-shaped cap 92, the cap having on a bottom side thereof a downwardly projecting annular flange 93 which can be inserted into the upper end of the upper portion 76 of the housing with a sufficiently tight frictional fit so that the cap 92 will not be forced off the upper end of the housing by any air pressure which may be present within the housing. The cap 92 has extending downwardly from the annular flange 93 a T-shaped cap retainer 94, the stem of the T-shaped cap retainer extending downwardly through the retaining wire 89 and the cross bar of the T-shaped retainer being longer than the distance between the legs of the retaining wire 89 so that it resists being pulled upwardly through the retaining wire 89. Thus, the cap 92 always remains with the housing, and cannot be inadvertently lost. The T-shaped cap retainer 94 has sufficient resilience so that, when the cap 92 is in the position shown in FIG. 5, the T-shaped cap retainer 94 will be urging the cap 92 toward a horizontal position in which the cap 92 is covering the upper end of the housing, in order to reduce the likelihood that fluids such as water or blood may enter the interior of the housing 76. The cap 92 has a radially outwardly projecting tab 96, which can best be seen in FIG. 7 and is used to manually lift the cap so that the flange 93 is extracted from the upper end of the upper portion 76.

Figure 7:
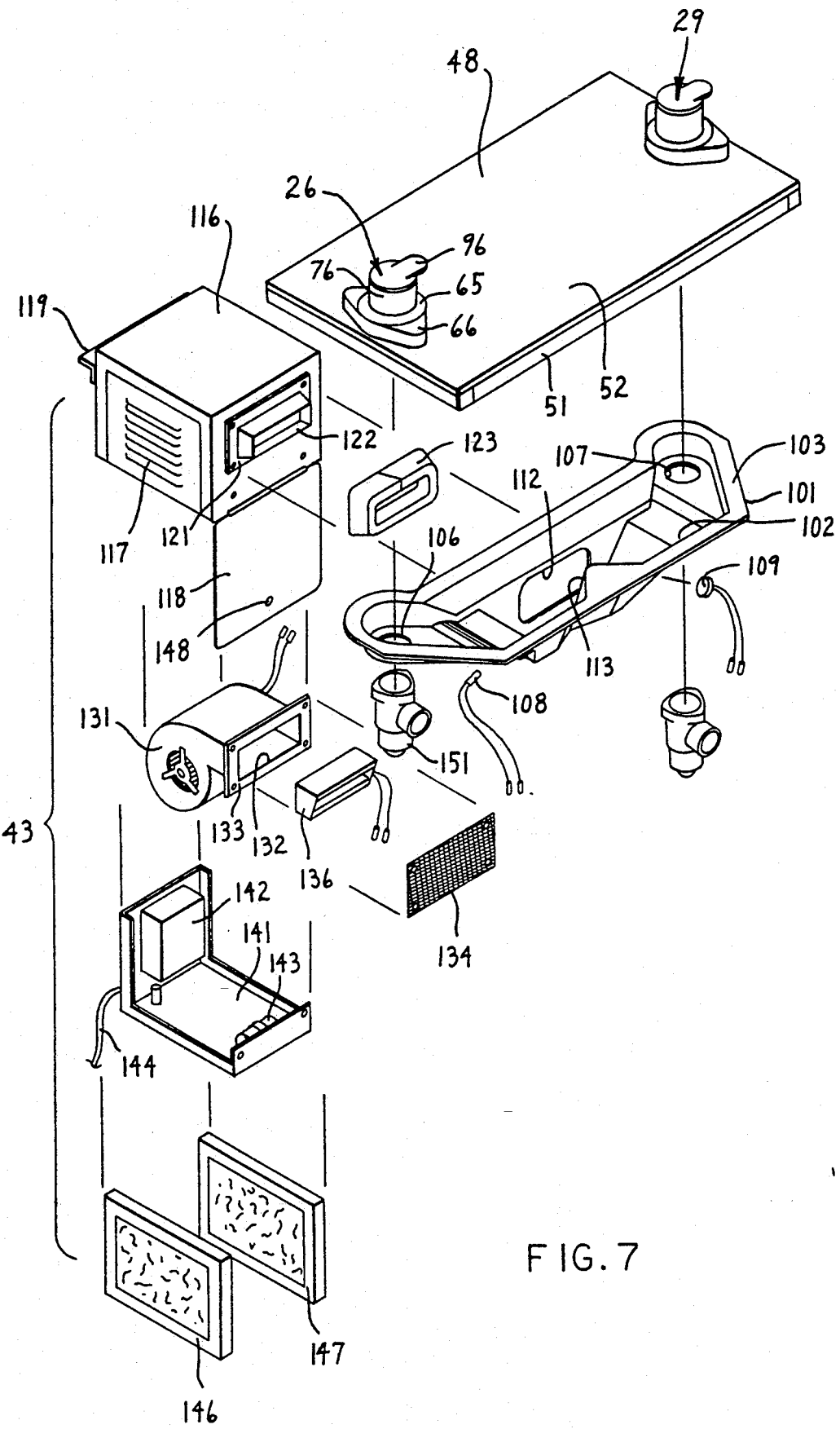
FIG. 7 is an exploded perspective view of the air supply system of the bed.

Referring to FIG. 7, the air supply system 43 includes an elongate plenum 101 which, in the preferred embodiment, is made from plastic or fiberglass and has therein an upwardly open air channel 102. The plenum 101 has an upwardly facing peripheral surface 103 extending all the way around the upper end of air channel 102. As shown in FIG. 4, the peripheral surface 103 is disposed against the underside of the support board 52, and is secured to the support board 52 by a plurality of conventional and not-illustrated rivets so as to effect a substantially airtight seal. If desired, a thin layer of a material such as rubber or foam can be provided between the peripheral surface 103 and the underside of the support board 52, in order to enhance the airtight seal between them.

As shown in FIG. 7, the bottom wall of the plenum 101 has at opposite ends two holes 106 and 107 which communicate with the air channel 102 and which are each disposed directly below a respective one of the housings 26 and 29, as also shown in FIG. 5. A thermistor 108 and a thermostat 109 are each mounted on the plenum so as to be exposed to the air within the air channel 102 through not-illustrated holes in the plenum. The plenum has intermediate its ends an approximately vertically extending wall portion having a rectangular air inlet opening 112 therethrough, and on an opposite side of air channel 102 from the inlet opening 112 is a V-shaped projection 113 which tends to split the air flow entering through the air inlet opening 112 so that respective portions of the air flow are directed to flow toward respective ends of the plenum 101.

Referring to FIGS. 6 and 7, the air supply system 43 also includes a metal housing 116 of generally rectangular shape, the housing 116 having air intake vents 117 in each of two opposite side walls thereof, having a bottom wall 118 pivotally supported by a hinge, having a flange 119 fixedly secured to a rear wall thereof, and having a portion 120 (FIG. 6) of the rear wall at the lower end thereof bent outwardly. An outlet plate which is a stamped metal part has a rectangular flange 121 disposed against and riveted to a front wall of the housing 116, and has a rectangular tubular projection 122 which serves as an air outlet and which converges in cross-sectional size in a direction away from the metal housing 116. A rubber strip 123 extends around the projection 122, the strip 123 being fixedly secured to the projection 122 by any suitable adhesive which is conventional and commercially available.

As shown in FIG. 6, the projection 122 and the rubber strip 123 thereon are disposed in the rectangular air inlet opening 112 in the plenum 101, the rubber strip 123 providing an airtight seal between the projection 122 and the plenum. The plenum thus supports the front end of the metal housing 116 by means of the projection 122. To support the rear end of the blower housing, a rubber shock absorber 126 is provided between the upper side of flange 119 and the underside of the frame 51, and the flange 119, shock absorber 126 and frame 51 are secured together by several bolts or rivets 127. It will thus be noted that the entire air supply system 43 moves with the thigh support section 48 as the thigh support section 48 is moved between its inclined and horizontal positions. Further, it will be noted that the rubber strip 123 and rubber shock absorber 126 minimize the extent to which vibrations are transferred from the housing 116 to the thigh section 48 of the patient support assembly 24.

Referring again to FIG. 7, an electric blower unit 131 having an integral motor and fan is disposed within the metal housing 116, and has an outlet opening 132 surrounded by a flange 133. In the preferred embodiment, the blower 131 is a conventional and commercially available forward curve centrifugal blower. A rectangular piece of conventional wire screen 134 is disposed between the blower flange 133 and the housing 116, and air from the blower can pass freely through the screen 134. The flange 133 of the blower 131, the screen 134, and the flange 121 of the outlet plate are each fixedly secured to the housing by a common set of not-illustrated rivets. An electric heater unit 136 of a conventional and commercially available type is disposed within the outlet opening of the blower 131, in order to heat the air being supplied from the blower 131 to the plenum 101. In the preferred embodiment the heater unit 136 is an 800 watt unit which has an internal thermostat to automatically shut it off if it overheats. The screen 134 is provided as a safety feature, in particular so that, in the event the hot coils of the heater unit 136 disintegrate, they will be contained within the blower 131 and will not be blown into the plenum 101 where they could present a fire hazard.

As shown in FIGS. 6 and 7, a metal chassis 141 is removably disposed within the housing 116, and has thereon a circuit board disposed beneath a cover 142. The cover 142 is entirely optional, and can in fact be omitted. A further circuit component 143 is also mounted on the chassis, and a cable 144 carries signals to and from the circuitry on chassis 141.

Two conventional air filters 146 and 147 are provided on opposite sides of the metal chassis 141, in order to filter air which enters through the air intake vents 117. In the preferred embodiment, the filters 146 and 147 have 0.2 micron filter elements. When the chassis 141 and the filters 146 and 147 are all properly inserted within the housing 116, the bottom wall 118 is pivoted from the open position shown in FIG. 7 to the closed position shown in FIG. 6, and is secured in the closed position of FIG. 6 by a single not-illustrated screw which extends through an opening 148 (FIG. 7) in the bottom wall 118 and which threadedly engages a not-illustrated threaded opening provided in the metal chassis 141.

It will be noted from FIG. 6 that the bent portion 120 of the housing 116 permits the cable 144 to extend away from the chassis 141 without interference from the housing when the bottom wall 118 is in its closed position. Further, portion 120 keeps fluids away from the end of the cable in order to avoid an electrical hazard.

Referring to FIG. 5, a T-shaped fixture 151 includes a portion 152 which is a vertically extending cylindrical tube having at its upper end an approximately triangular flange 153 (see FIG. 7). The flange 153 is fixedly secured to the plenum 101 by three screws 154 so that the opening through the tubular portion 152 is aligned with the opening 106 in the plenum. The fixture 151 also includes a horizontally extending branch tube portion 156 which communicates with the interior of the vertical tube portion 152 intermediate its ends. The vertical tube portion 152 has a threaded lower end 157 which is of smaller diameter than the remainder of tube 152.

Attached to the lower end of the fixture 151 is a valve 161, which includes a housing 162 having a cylindrical side wall 163 and a downwardly tapering conical bottom wall 164. The bottom wall 164 has an opening 166 at its lower end. The upper end portion 168 of the side wall 163 has a larger inside diameter than the remainder of the side wall 163, and has internal threads which engage the threads on the lower end of the fixture 151.

The side wall 163 has two notches 171 on diametrically opposite sides thereof which each open upwardly into the upper end portion of larger inside diameter, and a cylindrical pin 172 has each end disposed in a respective one of the notches 171. The ends of the pin are held in the notches by the lower end of the fixture 151. A ball 174 is vertically movably provided in the housing 162 below the pin 172, and in the preferred embodiment is a hollow plastic ball similar to a conventional ping pong ball. The ball 174 serves as a buoyant valve member. The diameter of the ball 174 is sufficiently large so that the ball 174 cannot move upwardly past the pin 172 on either side of the pin 172.

Referring to FIG. 4, a further T-shaped fixture 176 is provided below the housing 27, and is identical in structure to the fixture 151. The fixture 176 does not have a valve at its lower end, but instead has a cap 177 screwed onto the threads at its lower end. A flexible air tube 181, for example of the type having a helical wire concentrically disposed within a tubular plastic sheath, extends between the branch tubes of the fixtures 151 and 176, and has secured to each end a respective coupling tube 182 or 183 which tightly grips the branch tube of the associated fixture 151 or 176 in order to provide airtight connections.

On the opposite side of the bed, an arrangement symmetrically equivalent to that shown in FIG. 4 is provided for supplying air to the air outlet housings 28 and 29 (FIG. 2).

Figure 8:
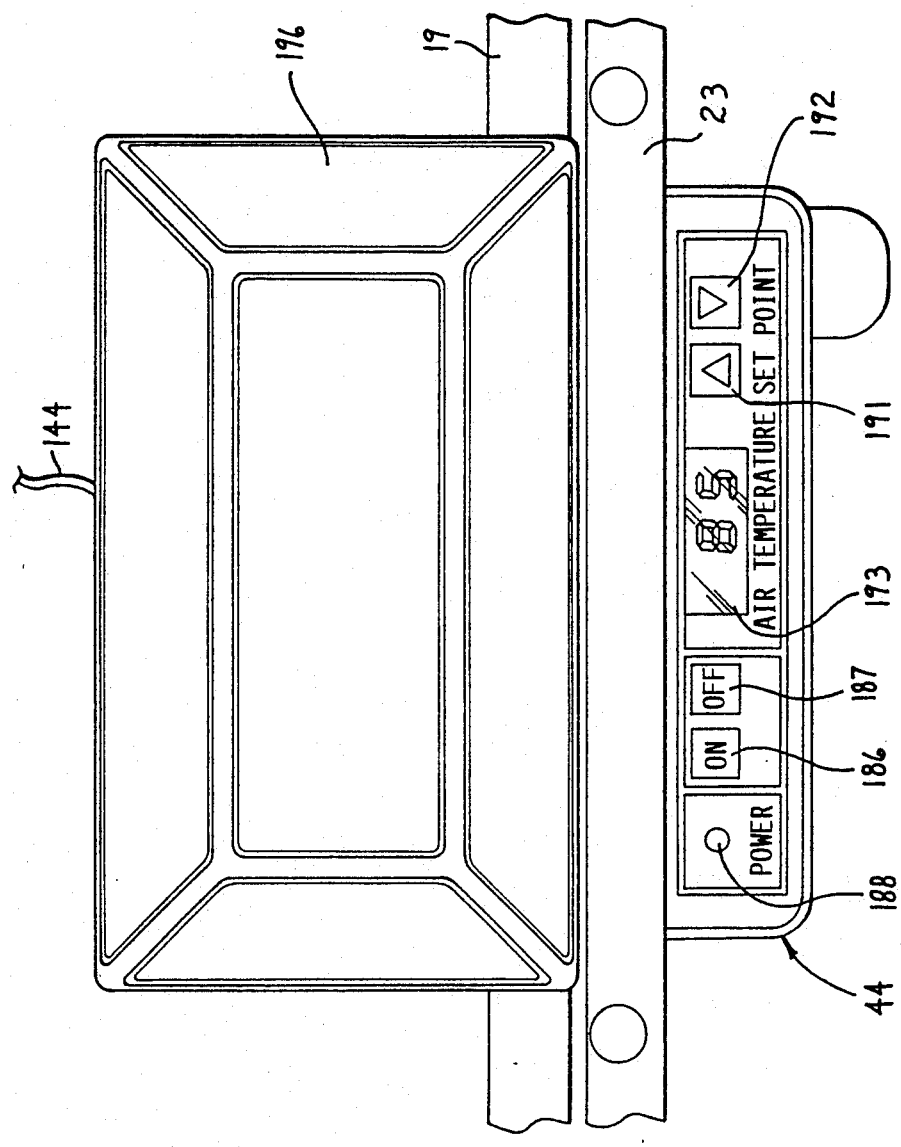
FIG. 8 is a top view of a control panel mounted at one end of the bed of FIG. 1.

The control panel 44 of FIG. 1 is shown in more detail in the top view of FIG. 8, and includes a power on push button 186, a power off push button 187, a power light emitting diode (LED) 188, a temperature up push button 191, a temperature down push button 192, and a digital display 193 showing a selected temperature. The control panel includes a housing 196 which is coupled by cable 144 to the air supply system, the housing 196 containing circuitry which is shown in diagrammatic form at the left end of FIG. 9.

Figure 9:
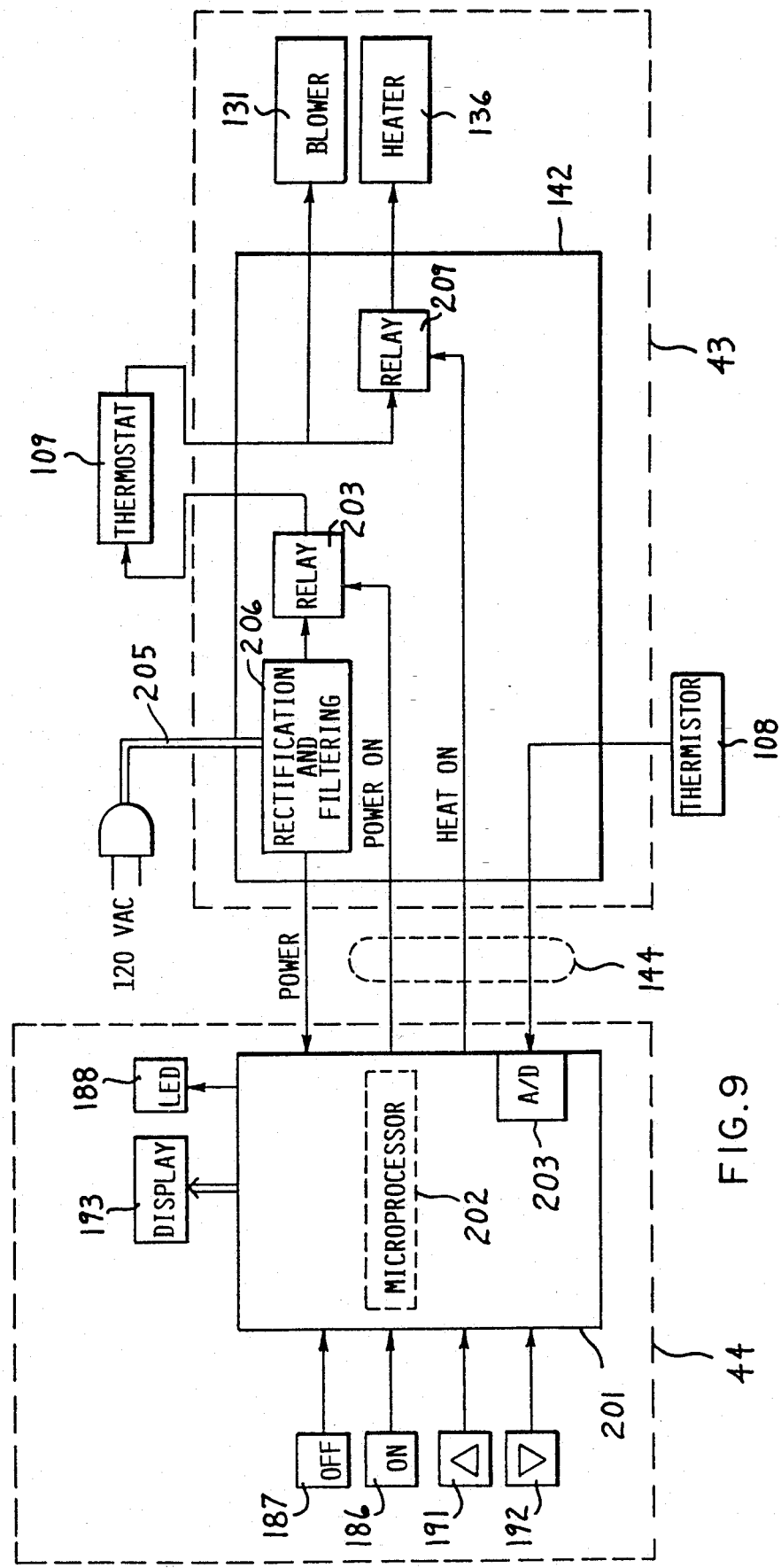
FIG. 9 is a schematic block diagram for a control circuit which is part of the bed of FIG. 1.

More specifically, referring to FIG. 9, the push buttons 186, 187, 191 and 192 are all connected to inputs of a circuit 201 which includes a conventional and commercially available microprocessor 202, and outputs of the circuit 201 control the display 193. The circuit 201 also includes an analog-to-digital (A/D) converter 203, which receives an analog signal through cable 144 from the thermistor 108 at the plenum 101, and converts the analog signal to a digital value. The circuit 201 produces a POWER ON output signal and a HEAT ON output signal, which are each supplied through cable 144 to the air supply system 43.

Still referring to FIG. 9, the air supply system 43 receives standard 120 volt AC line power through a line cord 205, and a conventional rectification and filtering circuit 206 uses the AC power to produce DC power at an appropriate voltage for the circuitry of the control panel 44 and the circuitry of the air supply system 43. Power is supplied from circuit 206 to the control panel 44 across a POWER line. The power from the circuit 206 is also supplied to a conventional relay 208. The relay 208 is controlled by the POWER ON line from the control panel 44. When the POWER ON line is actuated, the relay 208 supplies power through the thermostat 109 to the blower 131 and to a further relay 209. The relay 209 is controlled by the HEAT ON line from the control panel and, when the HEAT ON line is actuated, the relay 209 supplies power to the heater 136. As mentioned above, the heater 136 has an internal thermostat which prevents it from overheating. In addition, the thermostat 109 will automatically interrupt power to the blower 131 and heater 136 if the temperature in the plenum exceeds 140° F., in order to avoid a fire hazard and to prevent a patient from being burned by very hot air.

FIGS. 10 and 11 depict an inflatable underlay 212 which can be used in place of the mattress 33 and diffuser 42 shown in FIG. 1. The width of the underlay is slightly less than the distance between the air outlet housings 26 and 29, and the length of the underlay (when inflated) is approximately equal to the length of the patient support assembly 24. As shown in FIG. 11, the underlay 212 has an upper fabric sheet 213 and a lower fabric sheet 214 which are stitched to each other all along their peripheral edges. The sheets 213 and 214 are preferably made from the same tightly woven polyester fabric which was described above in association with diffuser member 42. A plurality of spaced and parallel seams 213 are provided at spaced locations along the underlay and extend in the width direction thereof, but the ends of the seams are spaced inwardly from the side edges of the underlay. On each side of the underlay 213, slightly offset from the longitudinal center of the underlay, is a respective air supply tube 218 or 219 which is made from the fabric of sheets 213 and 214, which communicates with the interior of the underlay, and which has at the outer end a hem containing an O-ring 221. The air supply tubes 218 and 219 are respectively inserted into the air outlet housings 26 and 29. Air is thus diffused through the fabric of the underlay 212 all around a patient lying on the underlay 212.

FIG. 12 discloses an overlay 226, which is similar in structure to the underlay 212 except that the air supply tubes 218 and 219 provided on the sides of the underlay 212 are omitted, and instead two similar air supply tubes 227 and 228 are provided at one end of the overlay 226. The spaced air supply tubes 227 and 228 are inserted into the housings 27 and 28 (FIG. 1). When the overlay 226 is used, the mattress 33 is also present, and a patient lays on the mattress 33 and the overlay 226 is placed over the patient. Again, air is diffused all around the patient through the fabric of the overlay 226.

Figure 13:
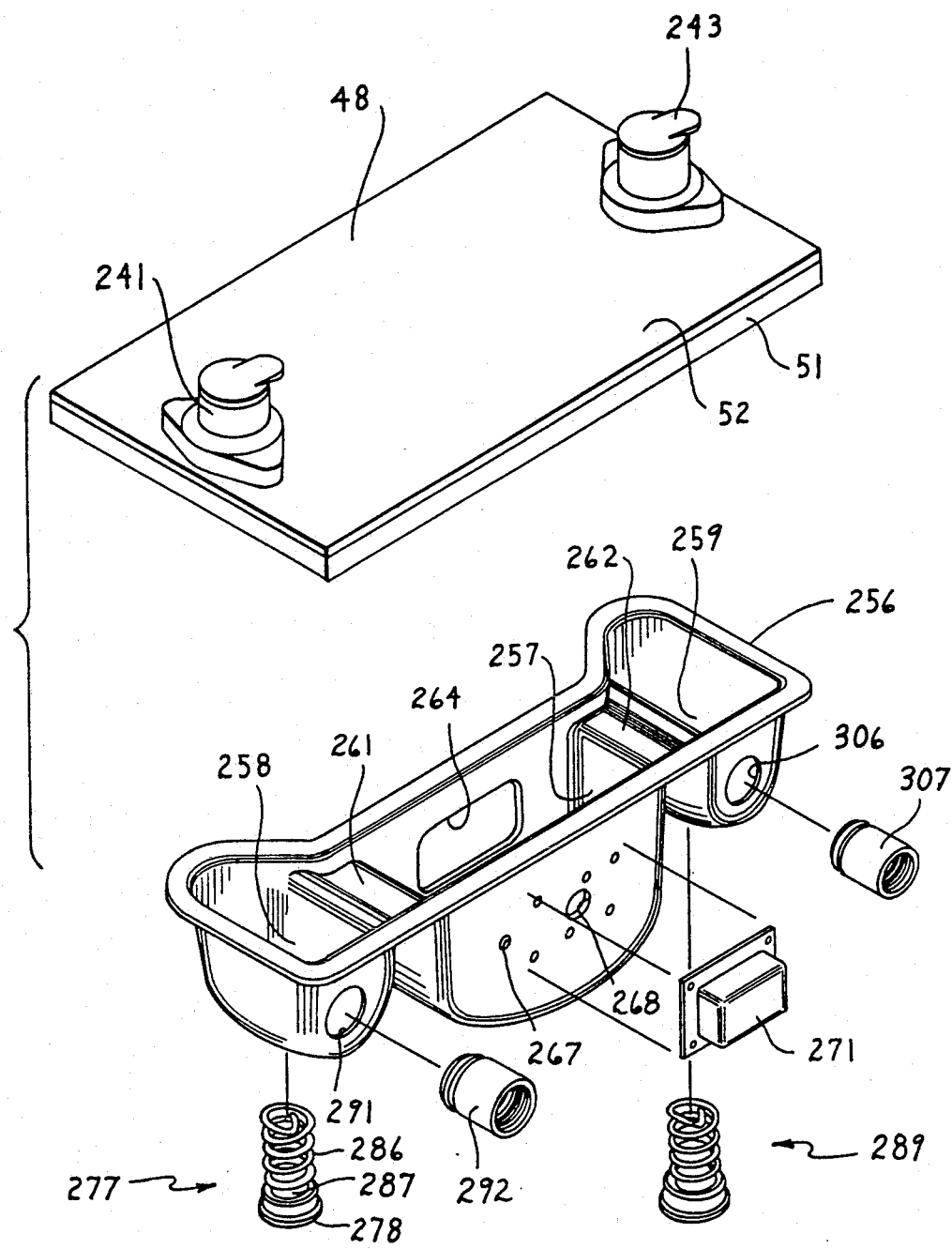
FIG. 13 is an exploded perspective view similar to a portion of FIG. 7 but showing an alternative embodiment of the illustrated structure.
Figure 14:
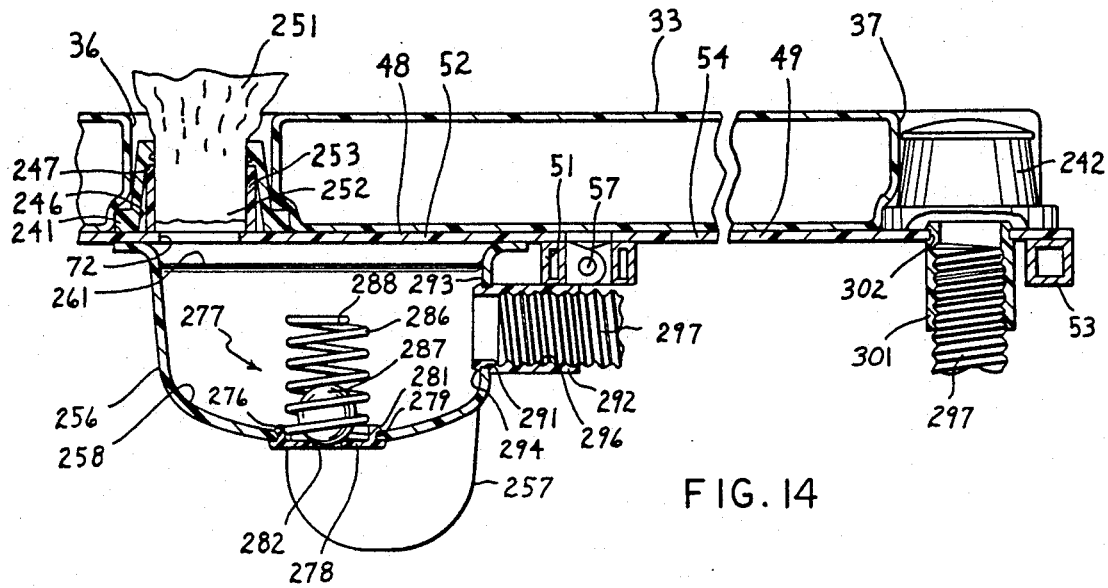
FIG. 14 is a sectional view similar to FIG. 4 but depicting the alternative embodiment of FIG. 13.
Figure 15:
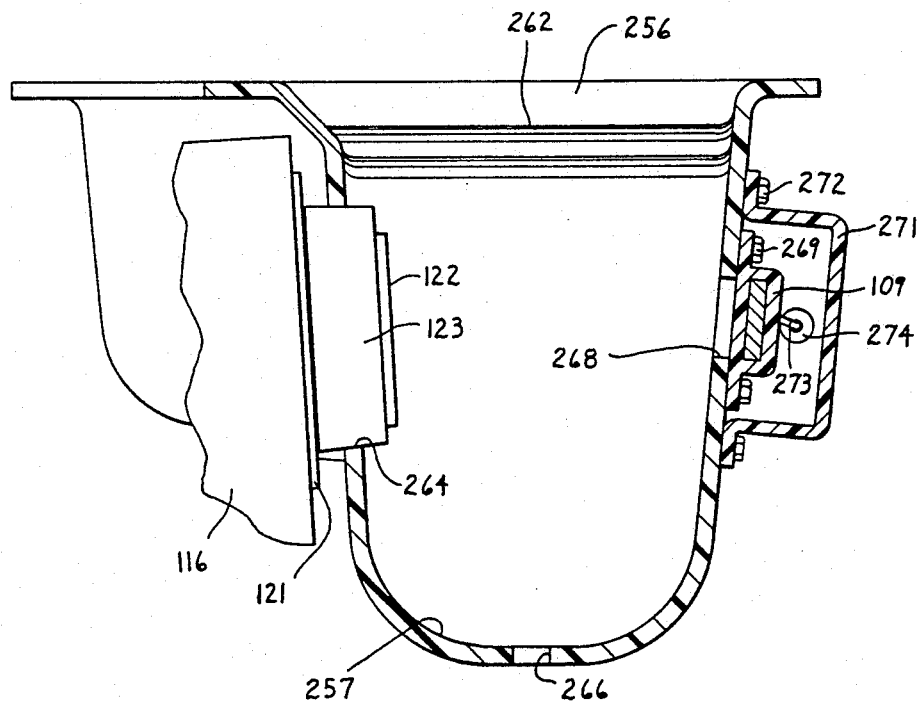
FIG. 15 is a central sectional side view of a plenum and associated components from the embodiment of FIG. 13.

FIGS. 13-15 depict an alternative embodiment of the hospital bed. Except for the differences described hereinafter, the embodiment of FIGS. 13-15 is identical to the bed of FIG. 1.

The bed of FIGS. 13-15 has four air outlet housings, three of which are visible in FIGS. 13 and 14 at 241, 242 and 243. The air outlet housings have approximately the same external shape and appearance as the air outlet housings 26-29 in the embodiment of FIG. 1, but internally are somewhat different, including the fact that the housings in FIGS. 13-15 do not have therein a wire grid equivalent to that shown at 81 in FIG. 5. More specifically, referring to FIG. 14, the air outlet housing 241 has on the interior thereof an upwardly converging frustoconical service 246, at the upper end of which is a downwardly facing and radially inwardly extending annular retaining surface 247. The lower end of the frustoconical surface 246 is adjacent the top surface of the support board 52 and is concentric to and spaced radially outwardly from the hole 72 through the support board 52. The cap for the housing and the arrangement which retains the cap on the housing are similar to those described in association with FIG. 5, and are therefore not described here in detail.

The embodiment of FIGS. 13-15 includes an elongate air dispersion member 251 which is similar to the air dispersion member 42 of FIG. 3 except that it is disposable and is made from paper rather than fabric. In particular, the air dispersion member 251 is made from a paper product having a conventional water barrier coating such as polyethylene, and having small holes punched in it in order to permit air to flow through the paper. Also, the open end of the dispersion member 251 does not have a rubber O-ring secured to it. Instead, the open end 252 of the dispersion member 251 is secured by a conventional and commercially available adhesive to the radially inwardly facing surface of a resiliently flexible cylindrical plastic sleeve 253. The sleeve 253 is removably inserted in the air outlet housing 241, the diameter and axial length of the plastic sleeve 253 being such that its upper end is disposed against the annular retaining surface 247 on the housing 241 and its lower end is disposed against the upper surface of the support board 52. In order to insert the sleeve 253 into the housing, the sleeve is manually compressed to a size and shape where it will fit through the opening at the upper end of the housing, and is then inserted through the opening and manually released, whereupon it resiliently returns to its normal shape and assumes the position shown in FIG. 14. The air dispersion member 251 could be tucked completely within the plastic sleeve 253 as the sleeve is inserted into the housing, and can thereafter remain in the sleeve until it is needed and withdrawn from the sleeve 253.

Referring momentarily to FIG. 7, the plenum 101 and the two T fixtures 151 have been replaced in the embodiment of FIGS. 13-15 with a single new integral plenum 256 formed from plastic using conventional vacuum techniques. The plenum 256 has in it a center well 257 disposed between two side wells 258 and 259, and upwardly facing horizontal surfaces 261 and 262 are provided between the center well and the respective side wells and are each spaced a short distance below the underside of the support board 52. The plenum 256 has between its ends and air inlet opening 264 which opens into center well 257 and which, as shown in FIG. 15, receives the air outlet projection 122 of the housing 116 having therearound the foam strip 123, in a manner analogous to that described for the previous embodiment. The plenum 256 has at the bottom of the center well 257 a small circular drain opening 266. The plenum 256 also has, in a side wall of the center well 257 opposite from the air inlet opening 264, an opening 267 in which the thermistor 108 can be removably mounted, and an opening 268 to provide air flow to the thermostat 109 (FIG. 15), the thermostat 109 being removably mounted on the plenum by bolts 269 as shown in FIG. 15 so as to cover the opening 268. A plastic thermostat cover 271 is provided over the thermostat 109 and is removably secured by bolts 272 to the plenum. The wires 273 for the thermostat 109 extending through a rubber grommet 274 provided in an opening in the wall of the thermostat cover 271. The thermostat operates at 110 volts AC, rather than at a low voltage, and the cover 271 is provided over the thermostat in order to prevent liquids from dripping on the thermostat and creating an electrical short which would constitute a safety hazard.

Referring to FIG. 14, the plenum 256 has at the bottom of the side well 258 a circular valve mounting hole 276, and a removable valve arrangement 277 is removably mounted in the hole 276. The valve arrangement 277 includes a circular cap having in a peripheral surface thereof an annular groove 279, the edges of the plenum material which define the hole 276 being received in the groove 279. An inclined surface 281 extends around the periphery of the cap adjacent its upper end, and facilitates insertion of the cap into the hole 276. The cap has through the center thereof a vertical drain opening 282. The valve arrangement 277 also includes a helical spring 286 having a diameter slightly less than that of the hole 276, the lower end of the spring 286 being fixedly secured to the upper end of the cap 278 and the spring having therein a hollow ball 287 which is similar to the ball 174 of FIG. 5 and which can move vertically within the spring between positions engaging and spaced upwardly from the drain opening 282 in the cap 278. The upper end 288 of the spring is bent so as to obstruct exit of the ball 287 from the upper end of the spring 286. The spring 286 thus does not technically function as a spring, but rather as a wire cage which guides movement of the ball 287.

The opposite side well 259 of the plenum 256 has at the lower end thereof a not-illustrated valve mounting hole which is comparable to the hole 276, and which has removably disposed therein a valve arrangement 289. The valve arrangement 289 is identical to the valve arrangement 277, and is therefore not described in detail here.

Referring to FIGS. 13 and 14, the side well 258 of the plenum 256 has in a sidewall thereof a circular connection opening 291. A cylindrical plastic coupling sleeve 292 has near one axial end a circumferential groove 293. When the coupling sleeve 292 is removably inserted into the connection opening 291, the groove 293 receives the material of the plenum which is adjacent and defines the connection opening 291. An annular inclined surface 294 is provided on the outer end of the sleeve 292 adjacent the groove 293 in order to facilitate insertion of the sleeve 292 into the opening 291. The sleeve 292 has in the interior thereof a helical groove which serves as a thread, and a flexible air tube 297 consisting of a helical wire surrounded by a plastic sleeve is screwed into the groove 296 in the sleeve 292. A conventional adhesive is provided between the air tube 297 and the sleeve 292 in order to fixedly secure the tube in the sleeve and in order to effect and air tight seal between them. As evident from FIG. 14, the opposite end of the air tube 297 has secured thereto a coupling sleeve 301 which is effectively identical to the coupling sleeve 292, and which is releasably coupled to a hole 302 provided through the support board 54 below the housing 242.

A mirror image arrangement of the air tube and coupling sleeves is provided on the opposite side of the bed, of which only a connection opening 306 (FIG. 13) for the side well 259 and a coupling sleeve 307 are depicted in the drawings.

Figure 16:
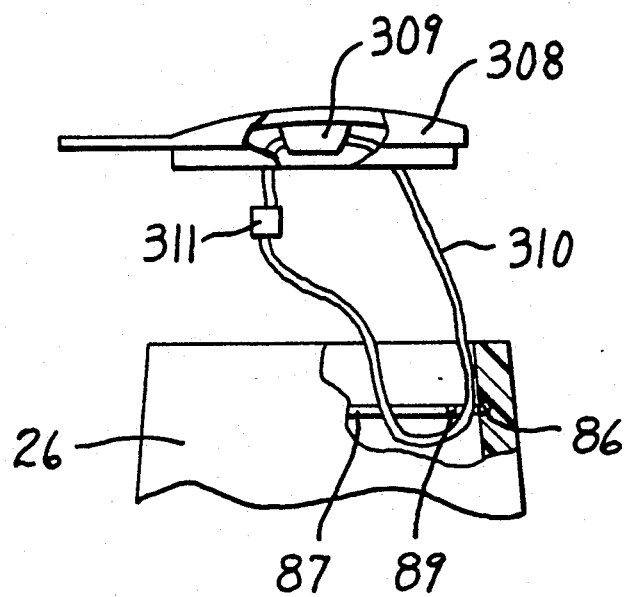
FIG. 16 is a fragmentary side view of an alternative embodiment of a housing and cap which are components of the embodiment of FIG. 1.

Turning to FIG. 16, an alternative embodiment of the cap for the housing 26 is depicted. The housing 26 itself is the same as described above, and includes the groove 86 containing the wire retainer 87 which includes the U-shaped retainer wire 89. The cap 308 is generally similar to the cap 92 shown in FIG. 5, except that the T-shaped retainer 94 has been omitted. Instead, and as shown in FIG. 16, the cap 308 has in the center of its underside a downward projection 309 which has a transverse hole therethrough. A flexible retaining element 310 is a loop which extends through the hole in the projection 309 and through the retaining wire 89 of the wire retainer 87. In the preferred embodiment, the retaining element is a conventional and commercially available plastic cable tie having at one end a connector 311 into which the opposite end is slidingly inserted in order to create a loop. Although the connector 311 inherently resists extraction of the end slidingly inserted therein, according to the invention the connector 311 is heat staked in order to positively prevent removal of the sliding end of the cable tie.

Whereas the T-shaped retainer 94 of FIG. 5 has inherent resiliency which tends to pull the cap 92 to a position covering the housing 26, the retaining element 310 of FIG. 16 does not have such inherent resiliency, and thus if the cap 308 is removed from and placed to the side of the housing, it will tend to remain there. This provides a degree of operator convenience, since it permits an air dispersion member to be more easily inserted or removed from the housing when the cap is not being resiliently urged to a position covering the housing.

OPERATION

Referring to the embodiment of FIGS. 1-9, when a patient is lying on the mattress 33, the air diffuser 42 can be manually positioned so as to be adjacent a portion of the patient's body to which it is desirable to supply temperature-controlled air. For example, the diffuser 42 may be placed to lay across the patient's knees, along the patient's leg, across the patient's ankles, or as otherwise appropriate to provide a supply of temperature-controlled air to a localized area. Each of the air outlet housings 27-29 preferably has a diffuser identical to the diffuser 42, and thus two or more diffusers could be simultaneously used where appropriate.

Referring to FIGS. 8 and 9, the push button 186 is pressed to cause the circuit 201 to actuate the POWER ON line, so that relay 208 is enabled and supplies power through the thermostat 109 to the blower 131 and relay 209. Then, the push buttons 191 and 192 are used to increase or decrease the selected temperature shown on the display 193 to a desired value. In FIG. 8, the display 193 is shown presenting an absolute temperature value, but it will be recognized that the display could also present relative temperature selections such as "low", "medium" and "high". Through the A/D converter 203, the circuit 201 monitors the output of the thermistor 108 disposed in the plenum 101, in order to determine the actual temperature of air being supplied to the plenum. The circuit 201 uses the temperature information from the thermistor to selectively turn the HEAT ON line on and off in order to alternately enable and disable the relay 209, to thereby actuate and deactuate the heater 136 in a manner so that the temperature of air supplied to the plenum is as close as possible to the selected temperature shown on the display 193. Referring to FIGS. 6 and 7, air drawn into the housing 116 through the vents 117 is filtered through the filters 146 and 147, and is then drawn into the blower 131 and forced through the heater 136, where it is heated if the heater 136 is actuated. Air exiting the heater 136 flows through the projection 122 and into the plenum 101, and is split by the V-shaped projection 113 into respective portions flowing outwardly in opposite directions within the plenum. The housings 26-29 each receive this heated air through the various channels and tubes described above. As to any housing which has its cap in place, the air does not exit the housing, but as to any housing which has its cap removed, the air flows upwardly out of the housing into the associated diffusion member 42.

Referring to FIG. 5, when a diffusion member 42 is not in use, it can be wadded up and manually tucked down into the upper portion 76 of its air outlet housing, the wire grid 81 preventing the diffuser 42 from dropping down into the plenum 101 obstructing air flow through the plenum. The flange 93 of cap 92 can be snugly inserted into the upper end of the air outlet housing in order to prevent any air from exiting the upper end of the housing when the diffuser for that housing is not being used.

When a diffuser 42 becomes soiled, the fabric at the end 62 of the diffuser is manually pinched so as to deform the O-ring 63 and dislodge it from the groove 77, and then the end 62 of the diffuser with the O-ring 63 is manually removed from the housing. Detachment of the diffuser in this manner takes only about one second. After the diffuser has been washed, its end 62 is inserted back into the housing until the O-ring 63 snaps back into the groove 77, which also only takes about one second.

As previously mentioned, the T-shaped cap retainer 94 has a certain amount of resilience which automatically urges the cap 92 toward a position covering the upper end of the housing, so that when the associated diffuser is tucked into the housing or has been removed from the housing, the housing will be covered in order to minimize the chance of a liquid such as blood or water dropping into the housing. Nevertheless, if a liquid does drop into the housing, it will pass downwardly through the plenum 101 and the fixture 151 to the valve 161. Whereas the hollow plastic ball 174 is normally urged downwardly by air pressure against the bottom wall of the valve housing in order to seal the opening 166 against air loss, the presence of any liquid will cause the ball 174 to float upwardly so that the air pressure within the air supply system forces the liquid out through the opening 166, after which the ball 74 will drop back down and seal the opening 166 again. Thus, the valve 161 substantially avoids air loss, while permitting liquids to be expelled from the air supply system during use of the air supply system without any adverse effect on the capability of the air supply system to supply air to the housings 26-29.

As to the underlay 212 shown in FIGS. 10 and 11 and the overlay 226 shown in FIG. 12, it is believed that the use of these components will be evident from the foregoing discussion, and a detailed discussion of their use is thus believed unnecessary here.

Turning to the embodiment of FIGS. 13-15, the basic operation is similar to that already described above for the first embodiment, and therefore a detailed discussion of the operation of the embodiment of FIGS. 13-15 is believed unnecessary. Nevertheless, a few brief comments are appropriate.

First, the provision of separate outer and center wells 257-259 for the plenum 256 help to prevent any liquid which may enter the plenum through the housings 241 and 243 from dispersing throughout the plenum. In particular, air can easily flow from the center well 257 to the side wells 258 and 259 above the surfaces 261 and 262, but liquid in the side wells 258 and 259 will be effectively maintained in the side wells, where the liquid can be discharged by the valve arrangements 277 and 289. To the extent that movement of the mobile bed causes some of the liquid in a side well 258 or 259 to slosh over one of the surfaces 261 and 262 into the center well 256, the liquid will quickly drain out of the center well through the small drain opening 266 (FIG. 15) at the bottom thereof.

In a situation where all of the air outlet housings have their caps installed so that there is no air flow out of the air outlet housings, the small drain opening 266 in the center well 257 permits a small amount of air to flow from the blower through the heater to the center well 257 and then out through the opening 266, to ensure that heat produced by the heater does not remain localized at the heater but instead moves into the center well 257 so that the thermistor 108 and thermostat 109 are exposed to the heat and thus the circuit of FIG. 9 can exercise a degree of feedback control over the heater and blower despite the fact that there is a minimal volume of air flow through the system when all of the housings have their caps in place.

With respect to the embodiment of FIG. 16, the retaining element 310 does not resiliently urge the cap 308 toward a position covering the housing 26, but aside from this the operation is the same as for the embodiment of FIGS. 1-12, and is therefore not described in detail here.

Although certain preferred embodiments of the invention have been described in detail for illustrative purposes, it will be recognized that there are variations or modifications of these preferred embodiments, including the rearrangement of parts, which lie within the scope of the appended claims. For example, it will be recognized that, while the disclosed embodiment is designed to provide a flow of heated air to a patient, the preferred embodiment could be modified so as to cool and/or dehumidify the air being supplied through a diffusion member to a patient.

The embodiments of the invention in which an exclusive property or privilege is claimed are defined as follows:

1. An apparatus comprising: a bed having an upwardly facing support surface; an air outlet device mounted on said bed; an elongate diffusion member having a proximate end operationally coupled to said air outlet device, said elongate diffusion member having means defining a flexible portion for facilitating movement of said diffusion member to a plurality of positions with respect to said support surface on said bed; and air supply means coupled to said air outlet device for supplying air to said proximate end of said diffusion member through said air outlet device, said air supplied to said diffusion member being diffused by said diffusion member into a region adjacent and external to said diffusion member, including diffusion of air from an interior to an exterior thereof through said flexible portion thereof.

2. An apparatus of claim 1, wherein said diffusion member is a hollow tube made of a sheet-like material which is air permeable, said tube being closed at a distal end thereof remote from said air outlet device.

3. An apparatus of claim 2, wherein said tube is made of a paper material.

4. An apparatus of claim 2, wherein said tube is made of a fabric.

5. An apparatus of claim 1, wherein said proximate end of said diffusion member is removably coupled to said air outlet device.

6. An apparatus of claim 1, wherein said air supply means is fixedly mounted on said bed.

7. An apparatus of claim 1, wherein said air supply means includes temperature adjusting means for effecting a change in the temperature of air supplied to said air outlet device.

8. An apparatus of claim 1, wherein said elongate diffusion member is flexible throughout substantially the entire length thereof.

9. An apparatus of claim 8, wherein said air supplied to said diffusion member is diffused therethrough along substantially the entire length thereof.

10. An apparatus comprising: a bed having an upwardly facing support surface; an air outlet device mounted on said bed; an elongate diffusion member having a proximate end operationally coupled to said air outlet device, said elongate diffusion member being movable to a plurality of positions with respect to said support surface on said bed; and air supply means coupled to said air outlet device for supplying air to said proximate end of said diffusion member through said air outlet device, said air supplied to said diffusion member being diffused by said diffusion member into a region adjacent and external to said diffusion member; wherein said diffusion member is a hollow tube made of a sheet-like material which is air permeable, said tube being closed at a distal end thereof remote from said air outlet device, wherein said tube is made of a paper material, wherein said air outlet device has an opening therein and has a retaining surface within said opening, and wherein said diffusion member includes a flexible sleeve extending around an opening at said proximate end thereof and secured to said tube, said sleeve being disposed within said opening in said air outlet device and said retaining surface engaging said sleeve and resisting withdrawal thereof from said air outlet device.

11. An apparatus comprising: a bed having an upwardly facing support surface; an air outlet device mounted on said bed; an elongate diffusion member having a proximate end operationally coupled to said air outlet device, said elongate diffusion member being movable to a plurality of positions with respect to said support surface on said bed; and air supply means coupled to said air outlet device for supplying air to said proximate end of said diffusion member through said air outlet device, said air supplied to said diffusion member being diffused by said diffusion member into a region adjacent and external to said diffusion member; wherein said diffusion member is a hollow tube made of a sheet-like material which is air permeable, said tube being closed at a distal end thereof remote from said air outlet device, wherein said tube is made of a fabric, wherein said air outlet device has an opening therein and an inwardly facing surface of said opening has a circumferential groove, and wherein said diffusion element includes said fabric having a hem sewn therein and extending around an opening at said proximate end thereof, and including in said hem a flexible O-ring which is removably received in said groove in said air outlet device.

12. An apparatus of claim 11, wherein said fabric is a tightly woven polyester material.

13. An apparatus of claim 12, wherein said polyester material has been treated with a fungicide and a bactericide.

14. An apparatus comprising: a bed having an upwardly facing support surface; and air outlet device mounted on said bed; an elongate diffusion member having a proximate end operationally coupled to said air outlet device, said elongate diffusion member being movable to a plurality of positions with respect to said support surface on said bed; and air supply means coupled to said air outlet device for supplying air to said proximate end of said diffusion member through said air outlet device, said air supplied to said diffusion member being diffused by said diffusion member into a region adjacent and external to said diffusion member; wherein said diffusion member is a hollow tube made of a sheet-like material which is air permeable, said tube being closed at a distal end thereof remote from said air outlet device, wherein said tube is made of a fabric, wherein said air outlet device has therein an opening, wherein said proximate end of said elongate diffusion member is disposed in said opening in said air outlet device, wherein said elongate diffusion member made of a fabric can be tucked into said opening in its entirety, and wherein said air outlet device includes a cap which can be moved to a position removably and sealingly covering said air outlet opening.

15. An apparatus comprising: a bed having an upwardly facing support surface; an air outlet device mounted on said bed and having therein an air outlet opening, said air outlet opening having in an inner surface thereof a circumferential groove; air supply means coupled to said air outlet device for supplying thereto air which is then emitted through said air outlet opening; and a diffusion member having a tubular air inlet portion which includes an open outer end encircled by a flexible annular retaining member removably disposed in said groove of said air outlet device.

16. An apparatus of claim 15, wherein said air inlet portion of said diffusion member is made of a fabric material having a hem sewn therein so as to encircle said open outer end thereof, said flexible annular retaining member being disposed in said hem.

17. An apparatus of claim 15, wherein said air outlet device includes a cap movable between a closed position in which said cap sealingly obstructs air flow through said opening in said air outlet device and an open position in which said cap is spaced from and permits air flow through said opening in said air outlet device.

18. An apparatus of claim 17, including retaining means for coupling said cap to said air outlet device in a manner preventing loss of said cap when said cap is in said open position.

19. An apparatus of claim 18, wherein said retaining means includes means for yieldably urging movement of said cap from said open position to said closed position.

20. An apparatus of claim 18, wherein said retaining means includes an annular groove provided in an inner surface of said air outlet opening of said air outlet device, a wire retaining element having a first portion of arcuate shape which is disposed in said groove and having a U-shaped second portion which has two spaced legs with their outer ends secured to said first portion and which projects inwardly into said air outlet opening, and includes a T-shaped retaining portion which is provided on said cap, which has a stem portion extending through said second portion of said wire retainer and has a cross bar at an outer end of said stem which has a length larger than the distance between the legs of said second portion of said wire retainer.

21. An apparatus of claim 20, wherein said cap includes a disk-like portion, includes an annular flange which projects outwardly from one side of said disk-like portion and has an outside diameter substantially equal to an inside diameter of said air outlet opening of said air outlet device to effect a secure frictional fit therebetween, and includes a tab projecting approximately radially outwardly from said disk-like portion.

22. An apparatus of claim 15, wherein said air outlet device has an upper portion which has said air outlet opening extending downwardly thereinto from an upper end thereof, said upper portion of said air outlet device being made of a resilient material which resiliently yields in response to the application of an approximately downward force thereto.

23. An apparatus of claim 22, including a cap movable to a closed position in which it effects an airtight seal of said air outlet opening in said air outlet device, said cap being made from a resiliently pliable material.

24. An apparatus of claim 15, wherein said diffusion member can be tucked in its entirety into said air outlet opening in said air outlet device.

25. An apparatus of claim 24, including means provided in said air outlet opening of said air outlet device at a location spaced from an outer end thereof for preventing movement of said diffusion member into said air outlet opening past said location.

26. An apparatus of claim 25, wherein said means for limiting movement of said diffusion member includes an inner surface of said air outlet opening having an annular groove, and includes a wire grid having an arcuate wire portion disposed in said annular groove and having a wire cross portion which extends transversely across said air outlet opening and has its opposite ends fixedly secured to said arcuate wire portion at spaced locations thereon.

27. An apparatus of claim 15, wherein said air outlet opening in said air outlet device extends approximately vertically and is open at its upper end, and including a valve disposed below said air outlet device and communicating with a lower end of said air outlet opening therein, said valve having an outlet opening providing communication between an interior and exterior of said valve, and having means for permitting fluid disposed within said valve to be discharged through said outlet opening while preventing pressurized air within said valve from flowing through said outlet opening.

28. An apparatus of claim 27, wherein said outlet opening opens vertically through a bottom wall of said valve, and wherein said valve includes a buoyant valve member movable between a position sealingly obstructing said outlet opening and a position spaced upwardly from said outlet opening.

29. An apparatus of claim 15, wherein said diffusion member is an elongate member having said air inlet portion at one end thereof, said elongate member being movable to a plurality of different positions with respect to a patient supported on said upwardly facing support surface.

30. An apparatus of claim 15, wherein said diffusion member is an inflatable underlay disposed on said patient support surface and adapted to have a patient lie thereon.

31. An apparatus of claim 15, wherein said diffusion member is an overlay which is disposed over a patient lying on said bed.

32. An apparatus comprising: a bed having an upwardly facing support surface; an air outlet device mounted on said bed and having therein an air outlet opening; air supply means for supplying air to said air outlet opening in said air outlet device; a diffusion member coupled to said air outlet device for receiving air through said air outlet opening therein and for diffusing said air to a region adjacent and external to said diffusion member, and means facilitating movement of said diffusion member between a storage position in which said diffusion member is tucked substantially in its entirety into said air outlet opening in said air outlet device and an operational position in which substantially all of said diffusion member is disposed outside of said air outlet opening in said air outlet device.

33. An apparatus comprising: a bed having an upwardly facing support surface; an air outlet device mounted on said bed and having therein an air outlet opening, said air outlet device having thereon a cap movable between a closed position in which said cap obstructs air flow through said air outlet opening and an open position in which said cap permits air flow through said air outlet opening, said air outlet device further including means for yieldably urging movement of said cap toward said closed position thereof; and air supply means for supplying air to said air outlet opening in said air outlet device.

34. An apparatus of claim 33, wherein said means for yieldably urging movement of said cap includes said cap having thereon a resilient retaining portion which has an outer end coupled to said air outlet device.

35. An apparatus of claim 34, wherein an inner surface of said air outlet opening in said air outlet device has an annular groove; including a retaining member which has an arcuate first wire portion disposed in said groove and which has a U-shaped second wire portion with two spaced legs having their outer ends fixedly secured to said first wire portion, said second wire portion projecting inwardly into said air outlet opening; and including said retaining portion of said cap being T-shaped, having a stem portion which extends through said second wire portion, and having a cross bar portion with a length greater than the distance between said legs of said second wire portion.

36. An apparatus comprising: a bed having an upwardly facing support surface; an air outlet device mounted on said bed and having therein an approximately vertically extending air outlet opening; air supply means for supplying air to said air outlet opening for discharge through an upper end thereof; and a valve provided below said air outlet device and communicating with a lower end of said air outlet opening, said valve having a fluid outlet opening and having means for facilitating a discharge of fluid disposed within said valve through said fluid outlet opening and for resisting the escape of air from the interior of said valve through said fluid outlet opening.

37. An apparatus of claim 36, wherein said fluid outlet opening extends downwardly from a lower portion of an interior region of said valve, and wherein said valve includes a buoyant member disposed within said interior region and movable between a position sealingly obstructing said fluid outlet opening and a position spaced upwardly from and permitting fluid flow through said fluid outlet opening.

38. An apparatus of claim 37, wherein said buoyant member is a hollow plastic ball.

39. An apparatus of claim 38, wherein said valve includes a removable cap having therethrough said fluid outlet opening and having supported thereon a helical retaining wire, said ball being movable within said retaining wire.

40. An apparatus of claim 37, wherein said valve includes a pin extending horizontally across said interior opening therein at a location above said buoyant member, said pin limiting upward movement of said buoyant member away from said fluid outlet opening.

41. An apparatus comprising: a bed having a support member which has thereon an upwardly facing support surface; first and second air outlet devices mounted at spaced locations on said support member, each said air outlet device having therein an air outlet opening; a plenum fixedly secured to said support member and having therein an air channel which is in fluid communication with said air outlet openings in each of said air outlet devices; and air supply means for supplying air to said plenum.

42. An apparatus of claim 41, wherein said plenum has an air inlet opening therein which communicates with said air channel therein; and wherein said air supply means includes a housing having on one side thereof a tubular air outlet projection and having means on an opposite side thereof for supporting said opposite side on said support member, wherein a piece of resilient material is provided around said air outlet projection, and said air outlet projection and said resilient material are snugly and air sealingly received within said air inlet opening in said plenum, said air supply means further including a blower disposed within said housing for supplying air to said air channel in said plenum through said air outlet projection of said housing.

43. An apparatus of claim 42, wherein said air supply means includes heater means disposed within said housing for heating air supplied by said blower to said air outlet projection.

44. An apparatus of claim 43, wherein said blower has an outlet opening, and wherein said heater means is disposed within said outlet opening of said blower.

45. An apparatus of claim 44, wherein said blower has a flange adjacent said outlet opening, wherein said housing includes a housing wall and includes an outlet part having a first portion which is said outlet projection and having a second portion which is a flange, said flanges on said blower and said outlet part being fixedly secured to said housing wall by a common rivet extending through said housing wall and each of said flanges.

46. An apparatus of claim 42, wherein said supply means includes filter means disposed within said housing for filtering air entering said housing before the air enters said blower.

47. An apparatus of claim 42, wherein said support member is movably supported on said bed, said air outlet devices, said plenum and said housing of said air supply system moving with said support member.

48. An apparatus of claim 41, wherein said plenum has therein an upwardly open channel which opens through an upper surface thereof, said upper surface having a peripheral portion which extends completely around said channel and is closely adjacent a surface of said support member, and including means facilitating a substantially airtight seal between said surface of said support member and said peripheral surface of said plenum.

49. An apparatus of claim 48, wherein said air outlet devices are provided on a side of said support member opposite from said plenum, and wherein said support member has two openings therethrough which each provide fluid communication between said channel in said plenum and the air outlet opening in a respective one of said air outlet devices.

50. An apparatus of claim 41, wherein said air outlet devices communicate with respective ends of an air channel in said plenum; wherein said plenum has an air inlet opening which opens transversely into said air channel between said ends of said channel; wherein said air supply means supplies air transversely into said air channel in said plenum through said air inlet opening in said plenum; and wherein said plenum has a V-shaped projection on a side of said channel opposite from said air inlet opening in order to split the incoming air flow from said air supply means into respective portions directed toward opposite ends of said channel.

51. An apparatus of claim 41, wherein said air outlet devices communicate with respective ends of an air channel in said plenum; wherein said plenum has an air inlet opening which opens transversely into said air channel between said ends of said channel; wherein said air supply means supplies air into said air channel in said plenum through said air inlet opening in said plenum; wherein said plenum has means defining respective side wells in said air channel at each end thereof; and including valve means in each said well for facilitating a discharge of liquid from the well while resisting the escape of air from said air channel.

52. An apparatus of claim 51, wherein said plenum has means defining a center well in said air channel between said side wells, said air channel providing communication between said center well and each said side well at upper ends thereof, and wherein said plenum has therethrough a drain opening which opens into said center well at a lower end thereof.

53. An apparatus of claim 41, wherein said air supply means includes temperature varying means for adjusting the temperature of air supplied to said plenum, said temperature varying means including temperature sensor means for measuring a temperature within said air channel in said plenum, and control means responsive to said temperature sensor means for controlling said temperature varying means in a manner causing air entering said plenum to be substantially at a predetermined temperature.

54. An apparatus of claim 53, including further means for sensing the temperature within said plenum and for disabling said temperature changing means when the air temperature in said plenum has passed a predetermined limit temperature.

55. An apparatus comprising: a bed having an upwardly facing support surface; two air outlet devices mounted on said bed at spaced locations; air supply means for supplying air to each of said air outlet devices; and a diffusion member which is physically separate from said bed and has two inlet portions which are each detachably coupled to a respective one of said air outlet device for receiving therefrom air from said air supply means, said diffusion member diffusing the air supplied thereto to a region adjacent and external to said diffusion member.

56. An apparatus of claim 55, wherein said air supply means is mounted in its entirety on said bed.

57. An apparatus of claim 55, wherein said air supply means includes heater means for heating said air supplied to said air outlet devices.

58. An apparatus of claim 55, wherein said diffusion member is an inflatable underlay disposed between a patient and said support surface on said bed.

59. An apparatus of claim 58, wherein said underlay includes upper and lower fabric sheets of generally rectangular shape which are secured to each other along their peripheral edges, and includes a plurality of spaced, parallel seams in said sheets which extend transversely to a lengthwise direction of said diffusion member and have ends spaced inwardly from the edges of said diffusion member, said inlet portions being disposed on opposite sides of said diffusion member at locations spaced from both ends of said diffusion member, and said inlet portions supplying air received from said air outlet housings to the region between said upper and lower sheets.

60. An apparatus of claim 55, wherein said diffusion member is an inflatable overlay adapted to be disposed over a patient supported on said support surface on said bed.

61. An apparatus of claim 60, wherein said overlay includes upper and lower fabric sheets of generally rectangular shape which are secured to each other along their peripheral edges, and includes a plurality of spaced, parallel seams in said sheets which extend transversely to a lengthwise direction of said diffusion member and have ends spaced inwardly from the edges of said diffusion member, said inlet portions being disposed at spaced locations along one end of said diffusion member, and said inlet portions supplying air received from said air outlet housings to the region between said upper and lower sheets.

62. An apparatus comprising: a bed having an upwardly facing support surface, an air outlet device which is mounted on said bed and which has therein an opening with a circumferential recess in an inwardly facing surface thereof; a diffusion member which includes a tubular inlet portion and an annular member provided at and extending around an opening at an outer end of said inlet portion, said annular member being removably received in said circumferential recess in said air outlet device; and air supply means coupled to said air outlet device for supplying air to said diffusion member through said air outlet device and said inlet portion of said diffusion member, said air supplied to said diffusion member being diffused by said diffusion member into a region adjacent and external to said diffusion member.

63. An apparatus of claim 62, wherein said circumferential recess in said inwardly facing surface of said opening is a circumferential groove, and wherein said annular member is a ring which is removable received in said groove.

64. An apparatus of claim 62, wherein said annular member is a substantially cylindrical sleeve which is removably received in said circumferential recess in said inwardly facing surface of said opening in said air outlet device.

65. An apparatus comprising: a diffusion member which is a hollow member made of a sheet-like material and which has a tubular inlet portion communicating at a first end with the interior of said diffusion member and having at a second end an annular member which extends around an opening through said inlet portion, said diffusion member having an air permeable portion, and said annular member being a substantially cylindrical sleeve having at an end thereof nearest said first end of said inlet portion an axially facing annular end surface.

66. An apparatus of claim 65, wherein said sleeve is flexible.

67. An apparatus of claim 66, wherein said sheet-like material is made of a paper material.

68. An apparatus comprising: a diffusion member which is a hollow member made of a sheet-like material and which has a tubular inlet portion communicating at a first end with the interior of said diffusion member and having at a second end a ring which extends around an opening through said inlet portion, said diffusion member having an air permeable portion.

69. An apparatus of claim 68, wherein said ring is a flexible O-ring, said inlet portion of said different member being made of a fabric and having a hem sewn therein which extends around said second end thereof, said flexible O-ring being disposed within said hem.

70. An apparatus comprising: A bed having an upwardly facing support surface, an air outlet device mounted on said bed and having therein an air outlet opening; means defining an air channel communicating at one end with said air outlet opening; air supply means for supplying air through said air channel to said air outlet opening for discharge through said air outlet opening; and a valve communicating with said air channel, said valve having a fluid outlet opening and having means for facilitating a discharge of fluid disposed within said valve through said fluid outlet opening and for resisting the escape of air from the interior of said valve through said fluid outlet opening.

71. An apparatus of claim 70, wherein said fluid outlet opening extends downwardly from a lower portion of an interior region of said valve, and wherein said valve includes a buoyant member disposed within said interior region and movable between a position sealingly obstructing said fluid outlet opening and a position spaced upwardly from and permitting fluid flow through said fluid outlet opening.

* * * * *

UNITED STATES PATENT AND TRADEMARK OFFICE
CERTIFICATE OF CORRECTION

PATENT NO. : 5,251,347
DATED : October 12, 1993
INVENTOR(S) : Christopher J. HOPPER et al It is certified that error appears in the above-identified patent and that said Letters Patent is hereby corrected as shown below:

On the title page, item [75], following "Kalamazoo County" insert:

---; Eugene D. Snook, Bedford Township, Calhoun County; Stephen C. Travis, Paw Paw Township, Van Buren County; Bradford D. Reed, Waverly Township, Van Buren County---.

Column 15, line 63; change "and" to ---an---.
Column 20, line 51; change "device" to ---devices---.

Signed and Sealed this

Fourteenth Day of June, 1994

Attest:

BRUCE LEHMAN

*Attesting Officer*    *Commissioner of Patents and Trademarks*